United States Patent [19]

Nohara

[11] Patent Number: 4,956,463

[45] Date of Patent: Sep. 11, 1990

[54] PYRIMIDONE COMPOUND AND PHARMACEUTICALLY ACCEPTABLE SALTS THEREOF

[75] Inventor: Fujio Nohara, Takaoka, Japan

[73] Assignee: Ikeda Mohando Company, Ltd., Toyama, Japan

[21] Appl. No.: 281,040

[22] Filed: Dec. 7, 1988

[30] Foreign Application Priority Data

Dec. 7, 1987 [JP] Japan .................. 62-309293

[51] Int. Cl.$^5$ .................. C07D 239/47; C07D 401/12; C07D 401/14; C07D 403/12
[52] U.S. Cl. .................................... 544/320; 544/321; 540/601
[58] Field of Search ................. 544/320, 321; 540/601

[56] References Cited

U.S. PATENT DOCUMENTS 4,710,498 12/1987 Nohara et al. ...................... 514/242

FOREIGN PATENT DOCUMENTS 0117345 5/1984 European Pat. Off. .
0186275 2/1986 European Pat. Off. .
59-7177 1/1984 Japan .

*Primary Examiner*—John M. Ford
*Attorney, Agent, or Firm*—Oblon, Spivak, McClelland, Maier & Neustadt

[57] ABSTRACT

A pyrimidone compound or a pharmaceutically acceptable salt thereof such as a 5,6-di-substituted-2-[4-<3-(1-piperidinomethyl)-phenoxyl>-cis-2-butenylamino]-4-(1H)-pyrimidone or a 5,6-di-substituted-2-[4-<4-(1-piperidinomethyl)-pyridyl-2-oxy>-cis-2-butenylamino]-4-(1H)-pyrimidone or a pharmaceutically acceptable salt thereof is herein disclosed. Such a compound or a salt thereof simultaneously shows gastric acid secretion inhibiting effect and gastric mucous membrane protecting effect and is useful as medicine for treating gastric diseases such as medicine for inhibiting gastric acid secretion or that for treating digestive ulcers.

11 Claims, No Drawings

PYRIMIDONE COMPOUND AND PHARMACEUTICALLY ACCEPTABLE SALTS THEREOF

BACKGROUND OF THE INVENTION

1. Field of the Invention

The present invention relates to a novel pyrimidone compound and more specifically to a useful and novel pyrimidone compound and pharmaceutically acceptable salt thereof exhibiting excellent gastric acid secretion inhibitory effect and cytoprotective effect.

2. Description of the Prior Art

Up to now, there have been known some pharmaceutically useful compounds which have excellent antagonistic effect in respect of $H_2$ receptor and gastric acid secretion inhibitory effect. For instance, Cimetidine, Ranitidine, Famotidine and Roxatidine are commercially available and many other compounds are disclosed in, for instance, Japanese Patent Unexamined Publication (hereunder referred to as "J.P. KOKAI") Nos. 60-255756; 61-85365; 61-207375 and 60-228465. One of principal effects of these compounds is acid secretion inhibitory effect due to antagonistic effect in respect of histamine $H_2$ receptor and they show a remarkable curative effect of gastric ulcers. However, if the medication is stopped after healing, such gastric ulcer recurs because of so-called rebound phenomenon, which becomes an important clinical problem. In order to prevent such gastric ulcer from recurring, an agent having acid secretion inhibitory effect such as an antagonist in respect of histamine $H_2$ receptor and a drug having a defence effect for the mucous membrane of alimentary canals have been simultaneously administered or after stopping the treatment with an antiulcer, the treatment is continued with a drug having defence effect. However, the use of only an attack factor inhibiting agent such as an acid secretion inhibitor is insufficient from the clinical point of view.

SUMMARY OF THE INVENTION

Accordingly, a principal object of the present invention is to provide novel pyrimidone derivatives and pharmaceutically acceptable salts thereof.

It is another object of the present invention to provide such a derivative or a salt thereof simultaneously having gastric acid secretion inhibiting effect and gastric mucous membrane protecting effect.

It is a further object of the present invention to provide such a derivative or a salt thereof which is useful as a drug for treating gastric diseases such as a drug for inhibiting gastric acid secretion or that for treating digestive ulcers and which shows only minor side effects.

The foregoing objects of the present invention can effectively be attained by providing a novel pyrimidone compound represented by the following formula (I) and pharmaceutically acceptable salts thereof:

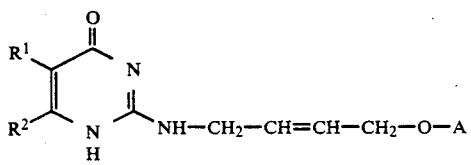
(I)

In the formula (I), $R^1$ and $R^2$ each represents a linear or branched alkyl group having 1 to 12 carbon atoms or a group represented by the formula:

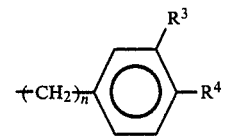

(wherein n is an integer of 1 to 3 and $R^3$ and $R^4$ each represents a hydrogen atom, an alkyl group having 1 to 6 carbon atoms, an alkoxy group having 1 to 6 carbon atoms or a methylenedioxy group); and A represents a group having the formula:

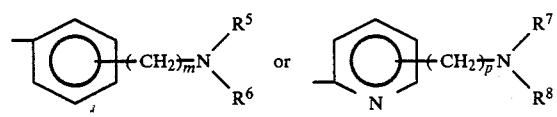

(wherein m and p each represents an integer of 1 to 3; and $R^5$ to $R^8$ each represents a hydrogen atom or a linear or branched alkyl group having 1 to 6 carbon atoms, or $-NR^5R^6$ and $-NR^7R^8$ each represents a group

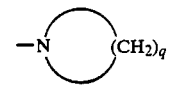

(wherein q is an integer of 4 to 6)).

DETAILED EXPLANATION OF THE INVENTION

The present invention will hereunder be explained in more detail.

Examples of an alkyl group having 1 to 12 carbon atoms shown as $R^1$ and $R^2$ in the formula (I) include methyl, ethyl, propyl, isopropyl, butyl, isobutyl, pentyl, isopentyl, hexyl, heptyl, octyl, decyl and dodecyl groups. Moreover, examples of an alkyl group having 1 to 6 carbon atoms shown as $R^3$, $R^4$, $R^5$, $R^6$, $R^7$ and $R^8$ include methyl, ethyl, propyl, isopropyl, butyl, isobutyl, pentyl and isopentyl groups.

In addition, the position of the substituent: $-(CH_2)_m-NR^5R^6$ in the formula:

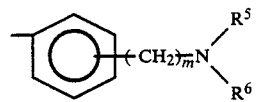

is preferably m- or p-position; and the group $-(CH_2)_p-NR^7R^8$ in the formula:

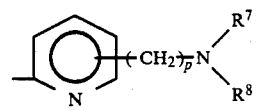

is preferably present at 4- or 6-position.

The compounds of the present invention represented by the formula (I) may be acid-addition salts and examples of acids which form salts with the compounds include inorganic acids such as hydrochloric acid, hydrobromic acid, sulfuric acid, nitric acid, phosphoric acid and methanesulfonic acid; and organic acids such as maleic acid, fumaric acid, oxalic acid, formic acid and acetic acid.

The novel compounds of the present invention represented by the formula (I) is prepared according to the following reaction scheme:

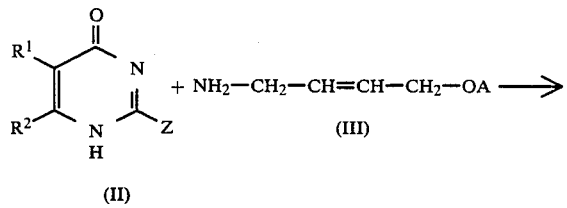

Compounds (I) + ZH

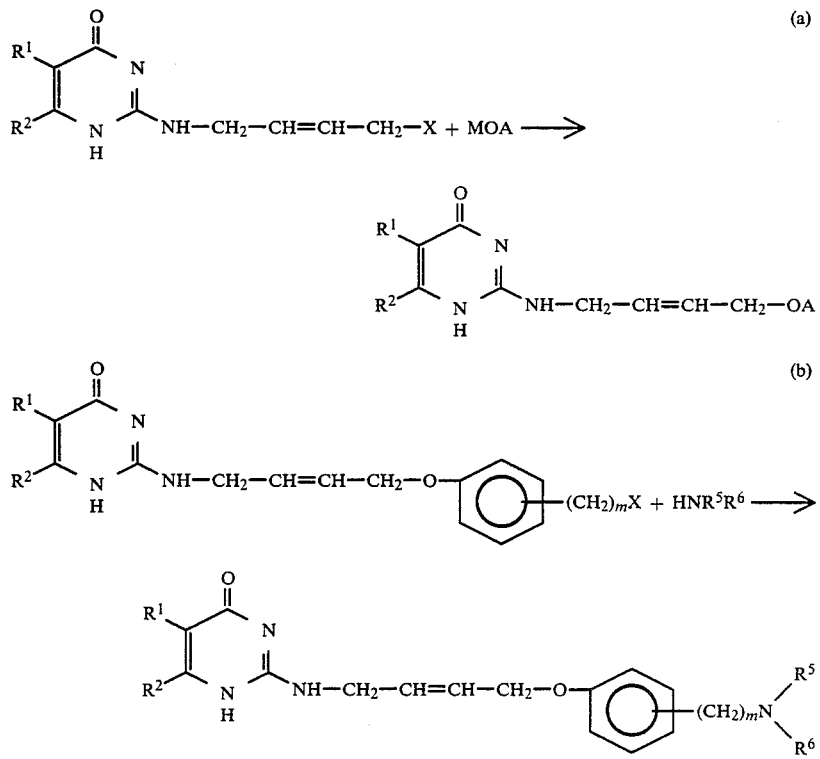

Wherein $R^1$, $R^2$ and A are the same as those defined above, and Z represents a nitroamino group, a lower alkylthio group or a lower alkoxy group.

Compounds (I) of the present invention can be prepared by reacting a compound represented by the formula (III), i.e., 4-(substituted aryloxy)-2-butenyl-amine derivative with a 2-nitroamino-, 2-lower alkylthio- or 2-lower alkoxypyrimidone derivative represented by the formula (II). Compounds (II) and (III) used as the starting materials are known ones. In other words, 2-nitroamino-4-(1H)-pyrimidone is prepared according to the method disclosed in J.P. KOKAI No. 60-228465, 2-methylthio-4-(1H)-pyrimidone is prepared according to the method disclosed in Yakugaku Zasshi, 1976, Vol. 96, No.3, p. 384, and 2-methoxy-4-(1H)-pyrimidone is prepared according to the method disclosed in Tetrahedron, 1984, Vol. 40, No. 17, p. 3313. On the other hand, starting material (III) includes cis- and trans- forms as the geometrical isomers and can be prepared according to the methods disclosed in J.P. KOKAI Nos. 57-165348; 61-85365; and 61-207375.

The reaction of compounds (II) and (III) can be performed without using a solvent, but it is desirable to use an inert organic solvent to control the reaction temperature. As such organic solvents, there may be used pyridine, picoline, quinoline, ethanol, toluene and xylene The reaction is preferably carried out while stirring under heating, preferably refluxing condition. It is desirable to control the reaction temperature to 50° to 200° C., preferably 80° to 150° C. Moreover, the reaction time ranges from 30 minutes to 50 hours, preferably 5 to 48 hours. In general, Compound (II) is reacted with an equimolar amount of Compound (III) and in particular it is preferred to use Compound (II) in a slightly excess amount.

Alternatively, the compounds of the present invention can also be prepared by the following reactions:

In the foregoing reaction schemes, X represents a halogen atom such as a chlorine, bromine or iodine atom; M is an alkali metal such as sodium or potassium; and m. $R^1$, $R^2$, $R^5$, $R^6$ and A are the same as those defined above.

The pharmacological effects of the compounds of the present invention will be detailed below. For this purpose, a variety of tests were carried out to compare some of the compounds of this invention with Cimetidine which has widely been employed clinically as a digestive antiulcer having an antagonistic effect for histamine $H_2$ receptor

(A) Inhibitory Effect on Gastric Acid Secretion by Histamine in its Pylorus Ligated Rat This test was carried out by an improved method of that reported by Watanabe et al., (OYO YAKURI (Applied Pharmacology), 1969, Vol. 3-1, pp. 7-14).

A male Wister rat having a body weight of about 160 g and which had not fed for 24 hours was anesthetized by an intraperitonea dose of 1.2 g/kg of urethane. After ligating of pylorus and esophagus, gaster anterior was incised and fitted with a double polyethylene wall cannula. The wall of the stomach was rinsed with saline (5 ml each) at 30 minutes intervals, and the amount of gastric acid present in the rinsing solution were determined by titration technique.

The basal amount of secreted gastric acid was initially measured three times, then 2 mg/kg of each of compounds of the invention was administered subcutaneously and 3 mg/kg of histamine was subcutaneously administered after the lapse of an additional 30 minutes.

The quantity of gastric acid secreted after the operation was measured continuously for 3 hours. Within that measurement interval, three time points at which the increase in acid secretion reached a maximum level were selected, and the average quantity of gastric acid secreted at those time points was taken as the increase in acid secretion, which was compared with the increase in acid secretion of the control group to calculate the percent inhibition for secretion of gastric acid.

Percent Inhibition of Gastric Acid Secretion (%) =

$$\left(1 - \frac{\text{Increase in Gastric Acid Secretion in Test Group}}{\text{Increase in Gastric Acid Secretion of Control Group}}\right) \times 100$$

The results obtained are listed in Table I in which the values found are expressed in the average of 5 measurements.

TABLE I

Inhibitory Effect on Gastric Acid Secretion Accelerated by Histamine in Pylorus-ligated Rats

| Compound | Gastric Acid Secretion in Rats | |
|---|---|---|
| | dose (mg/kg; s.c.) | Rate of inhibition (%) |
| Compound in Ex. 1 | 2 | 59** |
| Compound in Ex. 3 | 2 | 70** |
| Compound in Ex. 10 | 2 | 36** |
| Compound in Ex. 11 | 2 | 47** |
| Control (Cimetidine) | 2 | 70** |

Value affixed with  indicates that significant difference of $P < 0.01$ was observed as compared to the control group.

(B) Inhibitory Effect of the Compounds of the Present Invention on Ethanol-Induced Ulcer This test was performed in the manner similar to the method of Robert A. (Gastroenterology, 1975, Vol. 69, pp. 1045-1047). 30 mg/kg of the compound of this invention was orally administered to male Wister rats having a body weight of about 160 g after 24 hours fasting and after additional 30 minutes, 1 ml/animal of 100% ethanol was orally administered One hour after, the stomach was dissected out and was fixed with formalin, Then, the length of the hemorrhagic ulcers generated at the front portion of the stomach was measured by means of a microscope and these were defined as the coefficient of ulcer (U.C.).

$$\text{Percent Inhibition } (I.R.)(\%) = \left(1 - \frac{U.C. \text{ of Test group}}{U.C. \text{ of Control}}\right) \times 100$$

The results obtained are listed in Table II in which the values found are expressed in the average of 5 measurements.

TABLE II

Inhibitory Effect of the Compound of the Present Invention on Ethanol-Induced Ulcers

| Compound | I.R. of Ethanol-Induced Ulcer (%) (30 mg/kg; p.o.) |
|---|---|
| Compound of Ex. 1 | 65** |
| Compound of Ex. 3 | 80** |
| Compound of Ex. 7 | 61** |
| Compound of Ex. 10 | 73** |
| Compound of Ex. 11 | 79** |
| Compound of Ex. 13 | 56** |
| Compound of Ex. 14 | 87** |
| Compound of Ex. 16 | 58** |
| Compound of Ex. 17 | 78** |
| Compound of Ex. 18 | 45 |
| Control (Cimetidine) | −22.4 |

Value affixed with  indicates that significant difference of $P < 0.01$ was observed as compared to the control group.

(C) Test of Acute Toxicity of the Compounds of This Invention

Each test compound (500 mg/kg) was orally administered to ddy male mice having a body weight of about 22 g after 8 hours fasting and the general symptom and death or survival were observed The results observed are listed in Table III.

TABLE III

Mouse Acute Toxicity of the Compounds of the Present Invention Administrated Through P.O.

| Compound | Number of Death (dose = 500 mg/kg; p.o.) |
|---|---|
| Compound of Ex. 2 | 0/3 |
| Compound of Ex. 4 | ⅓ |
| Compound of Ex. 5 | ⅓ |

The compounds of the present invention exhibit inhibitory effect for gastric acid secretion accelerated due to the stimulation with histamine almost identical to that of Cimetidine as shown in Table I and simultaneously show a strong inhibitory effect for damages with ethanol which is not observed when Cimetidine is used, as shown in Table II.

Formulations comprising, as a principal component, the compounds represented by the general formula (I) and pharmaceutically acceptable salts thereof can be prepared by utilizing any known carriers and methods.

Such formulations may be administered orally or parenterally. The dose thereof varies depending on the conditions to be treated and age and sex of the individuals to be treated, but in general 10 to 500 mg per day for adults, which are preferably administered divisionally in 1 to 4 times.

The present invention will hereunder be explained in more detail with reference to the following non-limitative working Examples and the effects practically achieved will also be discussed in comparison with Comparative Examples In this connection, the synthetic scheme in Examples 1 to 4 are shown below:

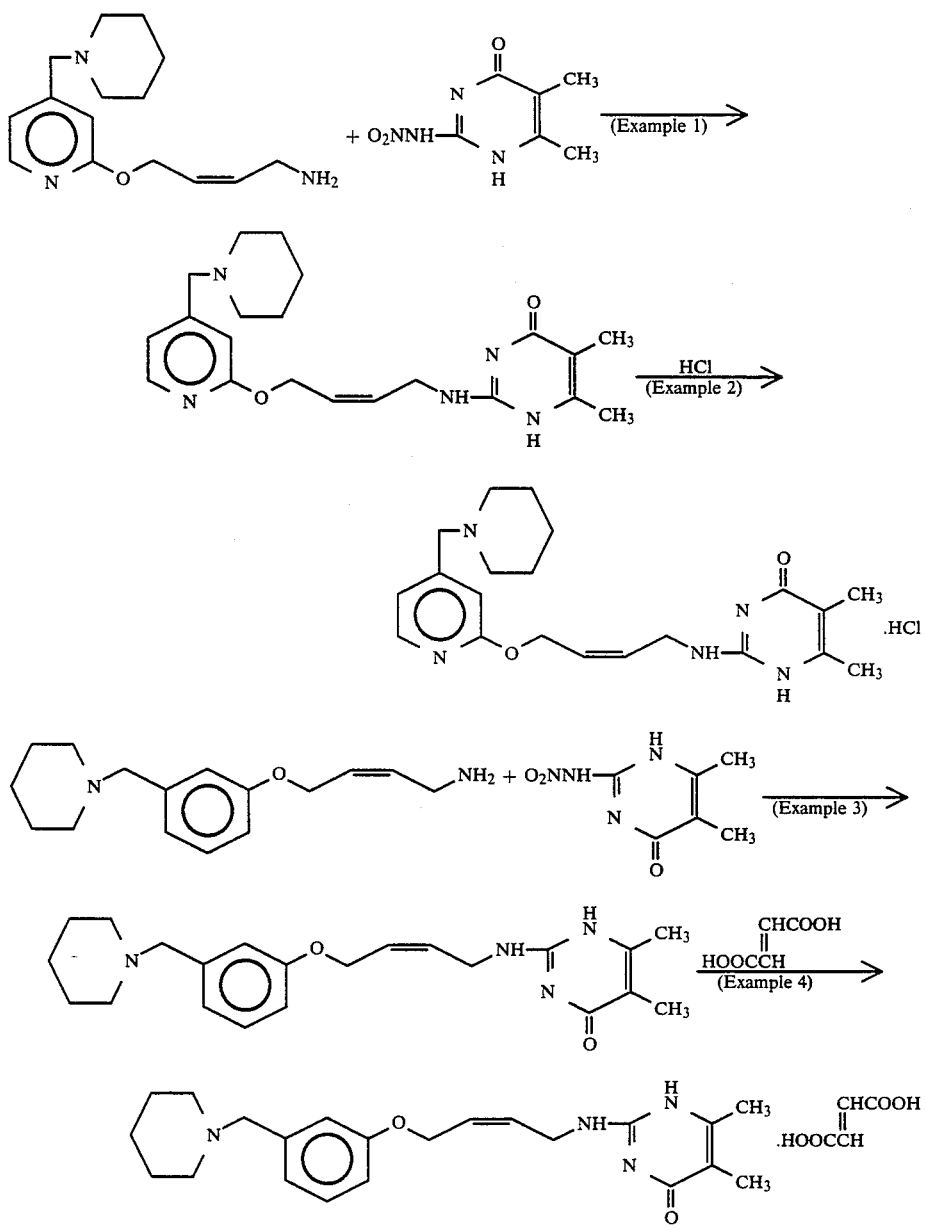

EXAMPLE 1:

5,6-Dimethyl-2-[4-<4-(1-piperidinomethyl)-pyridyl-2-oxy>-cis-2-butenylamino]-4-(1H)-pyrimidone 2.6 g of 4-<4-(1-piperidinomethyl)-pyridyl-2-oxy>-cis-2-butenylamine (this was prepared from 2-chloro-4-(1-piperidinomethyl) pyridine by the same method A disclosed in Example 1 of J.P. KOKAI No. 61-85365) and 2.0 of 5,6-dimethyl-2-nitroamino-4-(1H)-pyrimidone (this was prepared by the method disclosed in Reference Example of J.P. KOKAI No. 60-228465) were dissolved in 50 ml of pyridine and the resultant solution was stirred under refluxing for 15 hours. After completing the reaction, the solvent was distilled off in vacuo and the residue obtained was purified by silica gel chromatography (eluent: ethyl acetate/methanol/aqueous ammonia=6:1:1) to thus obtain 3.1 g of the title compound in an yield of 80.9%.

IR (liq. cm$^{-1}$): 3340, 2930, 1740, 1600, 1460, 1390, 1300, 1250, 1130, 1025, 1000, and 680.

NMR (CDCl$_3$, ppm): 1.2–1.7 (6H, m), 1.85 (3H, s), 2.15 (3H, s), 2.1–2.6 (4H, m), 3.3 (2H, s), 3.9–4.4 (2H, m), 4.8–5.1 (2H, d), 5.3–6.3 (4H, b), 6.6–7.0 (2H, t) and 7.9–8.2 (1H, d).

EXAMPLE 2:

5,6-Dimethyl-2-[4-<4-(1-piperidinomethyl)-pyridyl-2-ox-y>-cis-2-butenylamino]-4-(1H)-pyrimidone hydrochloride The oily product (14.1 g) obtained in Example 1 was dissolved in 100 ml of isopropanol and 3.2 ml of conc. HCl solution was added thereto to form pale yellow crystals. The crystals were recrystallized from isopropanol during which the treatment with active carbon was also carried out to obtain 11.5 g of colorless crystals having a melting point of 182°–4° C. (decomposed). Yield=74.2%.

IR (KBr, cm$^{-1}$): 3250, 2950, 2450, 1700, 1550, 1480, 1430, 1315, 1180, 1030, 950, 890, 830, 695 and 520.

NMR (DMSO-d$_6$, ppm): 1.4–2.1 (6H, m), 1.9 (3H, s), 2.25 (3H, s), 2.9–3.5 (4H, m), 4.0–4.4 (2H, m), 4.35 (2H, s), 4.8–5.2 (2H, m), 5.6–6.1 (2H, m), 7.2–7.5 (2H, t) and 8.2–8.4 (1H, d).

EXAMPLE 3:

5,6-Dimethyl-2-[4-<3-(1-piperidinomethyl)-phenoxy>-cis-2-butenylamino]-4-(1H)-pyrimidone The same procedures as in Example 1 were repeated except that 2.6 g of 4-<4-(1-piperidinomethyl-)-pyridyl-2-oxy>-cis-2-butenylamine were substituted for 2.6 g of 4-<3-(1-piperidinomethyl)-phenoxy>-cis-2-butenylamine to form 3.6 g of the title compound (yield=94.6%) as brownish oily product.

IR (liq. cm$^{-1}$) 3400, 2950, 1660, 1620, 1400, 1345, 1285, 1160, 1040, 990, 860, 780 and 700.

NMR (CDCl$_3$, ppm): 1.2–1.7 (6H, m), 1.85 (3H, s), 2.1 (3H, s), 2.2–2.5 (4H, m), 3.4 (2H, s), 3.9–4.2 (2H, m), 4.5–4.8 (2H, d), 5.5–6.0 (2H, m) and 4.6–7.3 (4H, m).

EXAMPLE 4:

5,6-Dimethyl-2-[4-<3-(1-piperidinomethyl)-phenoxy>-cis-2-butenylamino]-4-(1H)-pyrimidone fumarate 10 g of the oily product obtained in Example 3 were dissolved in 100 ml of isopropanol, to the resulting solution 3.03 g of fumaric acid were added and then heated to dissolve the same. The resulting solution was cooled to precipitate crystals and the crystals were recrystallized from water-containing isopropanol solution during which the solution was treated with active carbon to obtain 10.8 g (yield=82.8%) of colorless crystals M.P.=113°–117° C.

IR (KBr, cm$^{-1}$) 3250, 2950, 2700, 1620, 1450, 1360, 1260, 1180, 1030, 980, 780 and 670.

NMR (DMSO-d$_6$, ppm): 1.05–1.15 (2H, d), 1.3–1.8 (6H, m), 1.85 (3H, s), 2.1 (3H, s), 2.4–2.9 (4H, m), 3.75 (2H, s), 3.9–4.2 (2H, m), 4.6–4.9 (2H, m), 5.6–5.9 (2H, m), 6.65 (1H, s) and 6.75–7.9 (about 8H, m).

EXAMPLE 5:

5,6-Dimethyl-2-[4-<3-(1-piperidinomethyl)-phenoxy>-cis-2-butenylamino[-4-(1H)-pyrimidone hydrochloride

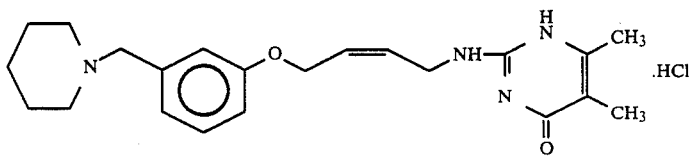

M.P.=92°–95° C.

IR (KBr, cm$^{-1}$) 3350, 2950, 2670, 1600, 1530, 1450, 1260, 1170, 1030, 950, 870, 780, 700 and 540.

NMR (DMSO-d$_6$, ppm): 0.9–1.15 (3H, d), 1.4–2.0 (9H, m), 2.1 (3H, s), 2.6–3.4 (4H, m), 3.85–4.2 (2H, m), 4.25 (2H, s), 4.1–4.9 (2H, m), 5.5–5.9 (2H, m) and 6.7–7.5 (4H, m).

EXAMPLE 6:

5-Pentyl-6-ethyl-2-[4-<3-(1-piperidinomethyl)-phenoxy>-cis-2-butenylamino]-4-(1H)-pyrimidone

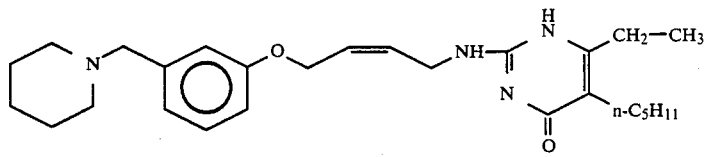

IR (liq, cm$^{-1}$) 3320, 2950, 2870, 1640, 1610, 1550, 1450, 1400, 1370, 1300, 1260, 1160, 1035, 860, 770, 695, 600 and 550.

NMR (CDCl$_3$, ppm): 0.5–1.9 (22H, m), 2.1–2.8 (4H, m), 3.5 (2H, s), 3.95–4.3 (2H, m), 4.6–4.9 (2H, m), 5.65–5.9 (2H, m) and 6.6–7.4 (4H, m).

EXAMPLE 7:

5-Heptyl-6-methyl-2-[4-<3-(1-piperidinomethyl)-phenoxy>-cis-2-butenylamino]-4-(1H)-pyrimidone

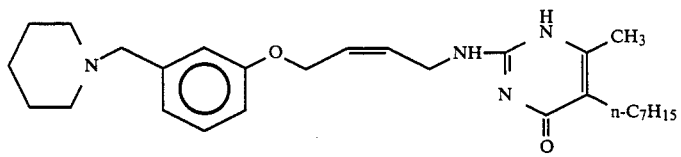

IR (liq, cm$^{-1}$) 3350, 2950, 1660, 1550, 1400, 1350, 1270, 1150, 1130, 1090, 1050, 990, 870, 780, 700, 640 and 560.

NMR (CDCl$_3$, ppm): 1.1–1.9 (19H, m), 2.0 (3H, s), 2.2 (2H, s), 2.2–2.7 (4H, m), 3.5 (2H, s), 3.9–4.3 (2H, m), 4.6–4.9 (2H, d), 5.6–6.0 (2H, m) and 6.6–7.4 (4H, m).

EXAMPLE 8:
5-Heptyl-6-methyl-2-[4-<4-(1-piperidinomethyl)-pyridyl-2-oxy>-cis-2-butenylamino]-4-(1H)-pyrimidone

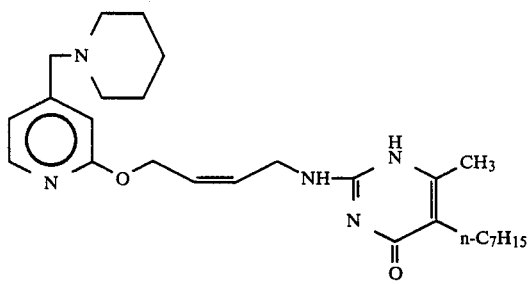

IR (KBr, cm$^{-1}$): 3350, 2950, 2880, 1650, 1615, 1560, 1480, 1350, 1305, 1150, 1040, 995, 880, 805, 780, 720 and 560.

NMR (CDCl$_3$, ppm): 0.5–1.8 (21H, m), 2.15 (3H, s), 2.1–2.6 (4H, m), 3.35 (2H, s), 3.8–4.9 (3H, m), 4.7–5.1 (2H, d), 5.5–5.9 (2H, m), 6.5–6.9 (3H, t) and 7.85–8.1 (2H, d).

Example 9: 5-Dodecyl-6-methyl-2-[4-(1-piperidinomethyl)-pyridyl-2-oxy>-cis-2-butenylamino]-4-(1H)-pyrimidone

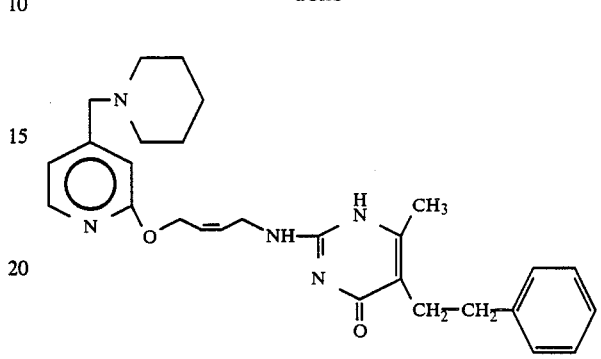

IR (KBr, cm$^{-1}$): 3350, 2930, 2870, 1640, 1615, 1560, 1480, 1290, 1150, 1120, 1040, 995, 870, 780, 720, 695 and 550.

NMR (CDCl$_3$, ppm): 0.6–1.8 (31H, m), 2.15 (3H, s), 2.1–2.6 (4H, m), 3.3 (2H, s), 3.9–4.3 (2H, m), 4.8–5.3 (3H, m), 5.5–5.9 (2H, m), 6.6–7.0 (3H, t) and 7.9–8.05 (1H, d).

Example 10: 5-Dodecyl-6-methyl-2-[4-<3-(1-piperidinomethyl)-phenoxy>-cis-2-butenylamino]-4-(1H)-pyrimidone

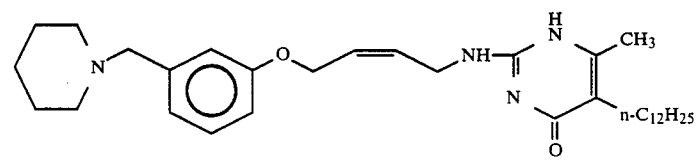

IR (KBr, cm$^{-1}$): 2950, 2520, 1700, 1610, 1500, 1460, 1300, 1260, 1170, 1030, 950, 795, 770, 710, 600 and 530.

NMR (CDCl$_3$, ppm): 1.6–2.0 (31H, m), 2.1 (3H, s), 2.1–2.55 (4H, m), 3.6 (2H, s), 4.1–4.4 (2H, m), 4.6–4.9 (2H, m), 5.6–5.9 (2H, s) and 5.8–7.8 (4H, m).

EXAMPLE 11:
5-Phenethyl-6-methyl-2-[4-<4-(1-piperidinomethyl)-pyridyl-2-oxy>-cis-2-butenylamino]-4-(1H)-pyrimidone ps M.P.=132°–138° C.

IR (KBr, cm$^{-1}$) 3350, 2950, 1650, 1607, 1480, 1400, 1290, 1245, 1030, 995, 870, 700, 670 and 550.

NMR (DMSO-d$_6$, ppm): 1.2–1.8 (6H, m), 1.95 (3H, s), 2.2–2.6 (4H, m), 2.4–2.8 (4H, m), 3.45 (2H, s), 3.9–4.25 (2H, m), 4.95–5.2 (2H, s), 5.5–6.0 (2H, m), 6.6–7.1 (2H, t), 7.3 (5H, s) and 8.0–8.25 (1H, d).

EXAMPLE 12:
5-Phenethyl-6-methyl-2-[4-<3-(1-piperidinomethyl)-phenoxy>-cis-2-butenylamino]-4-(1H)-pyrimidone

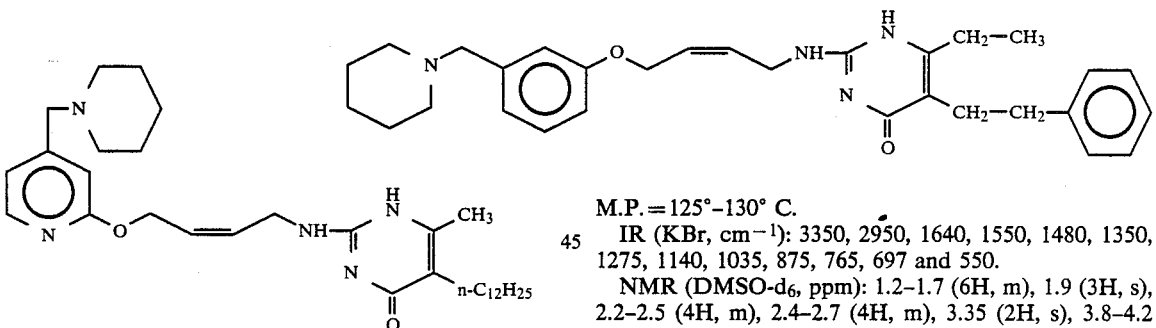

M.P.=125°–130° C.

IR (KBr, cm$^{-1}$): 3350, 2950, 1640, 1550, 1480, 1350, 1275, 1140, 1035, 875, 765, 697 and 550.

NMR (DMSO-d$_6$, ppm): 1.2–1.7 (6H, m), 1.9 (3H, s), 2.2–2.5 (4H, m), 2.4–2.7 (4H, m), 3.35 (2H, s), 3.8–4.2 (2H, m), 4.6–4.9 (2H, d), 5.6–5.9 (2H, m), 6.7–7.4 (4H, m) and 7.25 (5H, s).

EXAMPLE 13:
5-Benzyl-6-methyl-2-[4-<4-(1-piperidinomethyl)-pyridyl-2-oxy>-cis-2-butenylamino-4-(1H)-pyrimidone NMR (DMSO-d$_6$, ppm): 1.3–1.7 (6H, m), 2.1 (3H, s), 2.2–2.6 (4H, m), 3.4 (2H, s), 3.7 (2H, s), 3.8–4.2 (2H, m), 4.5–4.8 (2H, d), 5.5–5.9 (2H, m), 6.6–7.7 (4H, m) and 7.2 (5H, s).

Example 15: 5-(3,4-methylenedioxy)-benzyl-6-methyl-2-[4-<3-(1-piperidinomethyl)-phenoxy>-cis-2-butenylamino]-4-(1H)-pyrimidone

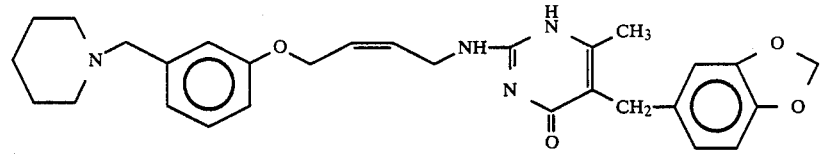

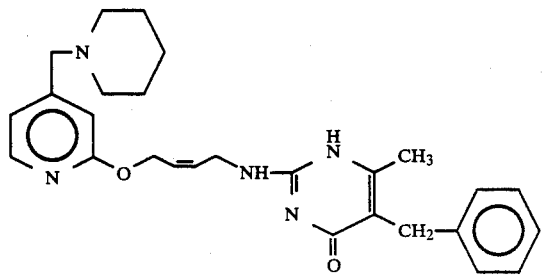

M.P.=112°–118° C.
IR (KBr, cm$^{-1}$) 3350, 2950, 1640, 1605, 1490, 1420,

M.P.=94°–102° C.
IR (KBr, cm$^{-1}$): 3350, 2950, 1640, 1610, 1495, 1450, 1350, 1240, 1035, 920, 795, 695, 640 and 560.
NMR (DMSO-d$_6$, ppm): 1.1–1.8 (6H, m), 2.05 (3H, s), 2.1–2.7 (4H, m), 3.35 (2H, s), 3.55 (2H, s), 3.8–4.2 (2H, m), 4.5–4.8 (2H, m), 5.5–5.6 (2H, m), 5.85 (2H, s) and 6.4–7.3 (7H, m).

EXAMPLE 16:
5-(3,4-methylenedioxy)-benzyl-6-methyl-2-[4-<4-(1-piperidinomethyl)-pyridyl-2-oxy>-cis-2-butenylamino]-4-(1H)-pyrimidone

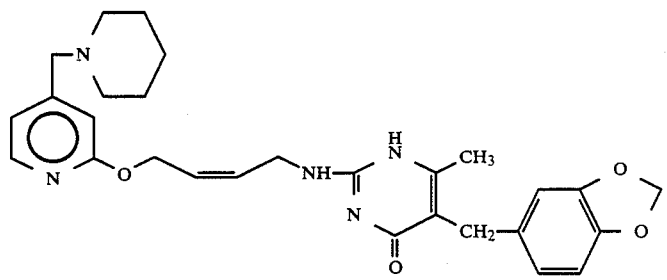

1400, 1350, 1285, 1140, 1040, 1000, 870, 780, 700, 640 and 560. NMR (DMSO-d$_6$, ppm): 1.2–1.8 (6H, m), 2.05 (3H, s), 2.1–2.6 (4H, m), 3.4 (2H, s), 3.7 (2H, s), 3.9–4.2 (2H, m), 4.85–5.1 (2H, d), 5.6–5.9 (2H, m), 6.6–7.0 (3H, t), 7.2 (5H, s) and 7.8–8.2 (1H, d).

EXAMPLE I4:
5-Benzyl-6-methyl-2-[4-<3-(I-piperidinomethyl)-phenoxy>-cis-2-butenylamino]-4-(1H)-pyrimidone M.P.=90°–100° C.
IR (KBr, cm$^{-1}$): 3350, 2950, 1650, 1615, 1490, 1290, 1240, 1040, 930, 800, 640 and 560.
NMR (DMSO-d$_6$, ppm): 1.1–1.7 (6H, m), 2.01 (3H, s), 2.1–2.5 (4H, m), 3.4 (3H, s), 3.6 (3H, s), 3.8–4.2 (2H, m), 4.8–5.1 (2H, d), 5.5–5.9 (2H, m), 5.9 (2H, s), 6.6–7.0 (5H, m) and 7.9–8.2 (1H, d).

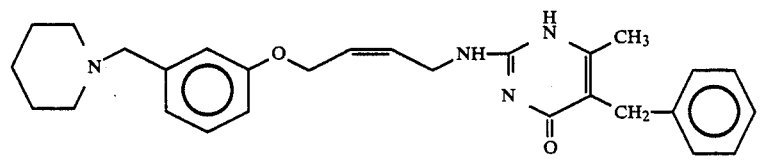

M.P.=109°–114° C.
IR (KBr, cm$^{-1}$): 3350, 2940, 1640, 1615, 1490, 1450, 1275, 1140, 1040, 770, 690 and 550.

EXAMPLE 17:
5-(p-methoxybenzyl)-6-methyl-2-[4-<3-(1-piperidinomethyl)-phenoxy>-cis-2-butenylamino]-4-(1H)-pyrimidone

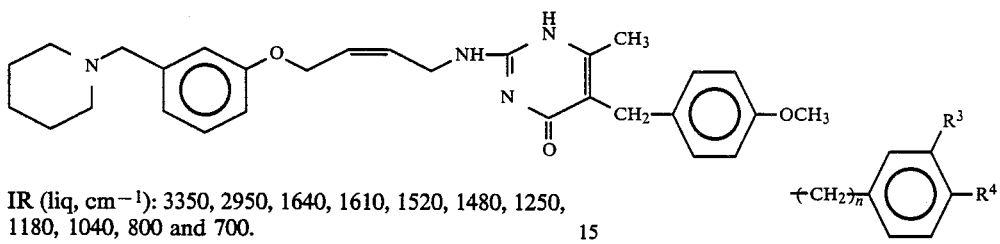

IR (liq, cm$^{-1}$): 3350, 2950, 1640, 1610, 1520, 1480, 1250, 1180, 1040, 800 and 700.

NMR (DMSO-d$_6$, ppm): 1.2–1.7 (6H, m), 1.8 (3H, s), 2.0 (3H, s), 2.1–2.7 (4H, m), 3.4 (2H, s), 3.7 (3H, s), 3.8–4.3 (2H, m), 4.6–4.9 (2H, m), 5.5–5.8 (2H, m) and 6.4–7.5 (8H, m).

EXAMPLE 18:
5-(3,4-methylenedioxy)-benzyl-6-n-propyl-2-[4-3-(1-piperidinomethyl)-phenoxy>-cis-2-butenylamino>-4-(1H)-pyrimidone

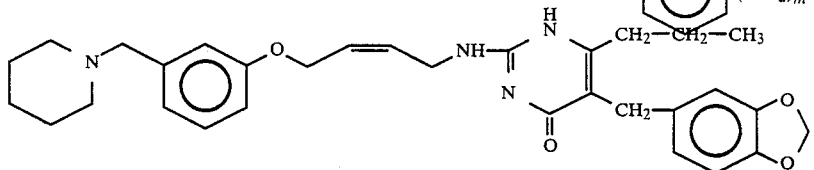

IR (liq, cm$^{-1}$): 3350, 2960, 2800, 1660, 1390, 1340, 1160, 1120, 1040, 990, 922, 870, 790, 770, 695, 630 and 500.

NMR (CDCl$_3$, ppm): 0.6–1.1 (3H, t), 1.1–1.9 (8H, m), 1.95 (3H, s), 2.2–2.6 (4H, m), 3.45 (2H, s), 3.7 (2H, s), 3.8–4.1 (2H, m), 4.5–4.75 (2H, d), 5.5–5.8 (2H, m), 5.9 (2H, s) and 6.6–7.4 (7H, m).

EXAMPLE 19: 5,6-Dimethyl-2-[4-<3-(1-piperidinomethyl)-phenoxy>-cis-2-butenylamino]-4-(1H)-pyrimidone dihydrochloride

M.P.=204°–206° C.

IR (KBr, cm$^{-1}$): 3350, 2750, 1670, 1600, 1460, 1250, 1170, 1035, 950, 860, 795, 690 and 535.

EXAMPLE 20:
5,6-Dimethyl-2-[4-<4-(1-piperidinomethyl)-pyridyl-2-oxy>-cis-2-butenylamino]-4-(1H)-pyrimidone dihydrochloride

M.P.=275°–278° C.

IR (KBr, cm$^{-1}$): 3300, 2970, 1640, 1560, 1410, 1300, 1170, 1060, 859, 800, 642 and 558.

What is claimed is:

1. A pyrimidone compound represented by the formula (I) or a pharmaceutically acceptable salt thereof:

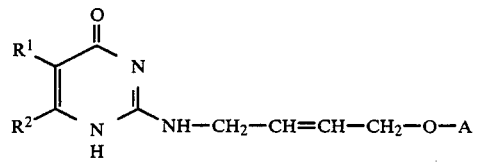

wherein R$^1$ and R$^2$ each represents a linear or branched alkyl group having 1 to 12 carbon atoms or a group represented by the formula:

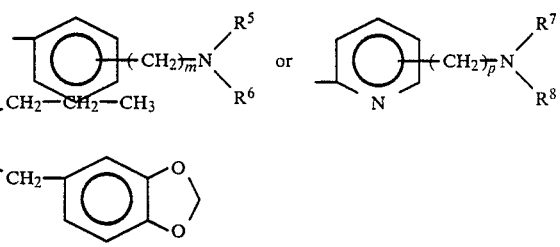

wherein n is an integer of 1 to 3 and R$^3$ and R$^4$ each represents a hydrogen atom, an alkyl group having 1 to 6 carbon atoms, an alkoxy group having 1 to 6 carbon atoms or a methylenedioxy group; and A represents a group having the formula:

wherein m and p each represents an integer of 1 to 3; and R$^5$ to R$^8$ each represents a hydrogen atom or a linear or branched alkyl group having 1 to 6 carbon atoms, or —NR$^5$R$^6$ and —NR$^7$R$^8$ each represents a group of the formula:

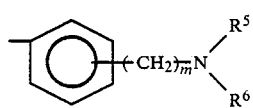

wherein q is an integer of 4 to 6.

2. The pyrimidone compound or a pharmaceutically acceptable salt thereof as set forth in claim 1 wherein the alkyl group having 1 to 12 carbon atoms as shown R$^1$ and R$^2$ is selected from the group consisting of methyl, ethyl, propyl, isopropyl, butyl, isobutyl, pentyl, isopentyl, hexyl, heptyl, octyl, decyl and dodecyl groups; the alkyl group having 1 to 6 carbon atoms as shown R$^3$ to R$^8$ is selected from the group consisting of methyl, ethyl, propyl, isopropyl, butyl, isobutyl, pentyl and isopentyl groups; the position of the substituent —(CH$_2$)$_m$—NR$^5$R$^6$ in the formula:

is m- or p-position; and the group —(CH$_2$)$_p$—NR$^7$R$^8$ in the formula:

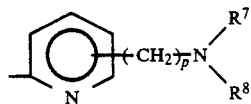

is present at 4- or 6-position.

3. The pyrimidone compound or a pharmaceutically acceptable salt thereof as set forth in claim 1 wherein the salt is an acid-addition salt with hydrochloric acid, hydrobromic acid, sulfuric acid, nitric acid, phosphoric acid, methanesulfonic acid, maleic acid, fumaric acid, oxalic acid, formic acid or acetic acid.

4. The pyrimidone compound or a pharmaceutically acceptable salt thereof as set forth in claim 1 wherein the compound is a 5,6-di-substituted-2-[4-<3-(1-piperidinomethyl)-phenoxy>-cis-2-butenylamino]-4-(1H)-pyrimidone or pharmaceutically acceptable salts thereof.

5. The pyrimidone compound or a pharmaceutically acceptable salt thereof as set forth in claim 4 wherein the compound is 5,6-dimethyl-2-[4-<3-(1-piperidinomethyl)-phenoxy>-cis-2-butenylamino]-4-(1H)-pyrimidone hydrochloride.

6. The pyrimidone compound or a pharmaceutically acceptable salt thereof as set forth in claim 4 wherein the compound is 5,6-dimethyl-2-[4-<3-(1-piperidinomethyl)-phenoxy>-cis-2-butenylamino]-4-(1H)-pyrimidone dihydrochloride.

7. The pyrimidone compound or a pharmaceutically acceptable salt thereof as set forth in claim 1 wherein the compound is 5,6-dimethyl-2-[4-<3-(1-piperidinomethyl)-phenoxy>-cis-2-butenylamino]-4-(1H)-pyrimidone fumarate.

8. The pyrimidone compound or a pharmaceutically acceptable salt thereof as set forth in claim 1 wherein the compound is a 5,6-di-substituted-2-[4-<4-(1-piperidinomethyl)-pyridyl-2-oxy>-cis-2-butenylamino]-4-(1H)-pyrimidone or a pharmaceutically acceptable salt thereof.

9. The pyrimidone compound or a pharmaceutically acceptable salt thereof as set forth in claim 8 wherein the compound is a 5,6-dimethyl-2-[4-<4-(1-piperidinomethyl)-pyridyl-2-oxy>-cis-2-butenylamino]-4-(1H)-pyrimidone or pharmaceutically acceptable salts thereof.

10. The pyrimidone compound or a pharmaceutically acceptable salt thereof as set forth in claim 9 wherein it is a 5,6-dimethyl-2-[4-<4-(1-piperidinomethyl)-pyridyl-2-oxy>-cis-2-butenylamino]-4-(1H)-pyrimidone hydrochloride.

11. The pyrimidone compound or a pharmaceutically acceptable salt thereof as set forth in claim 9 wherein the compound is a 5,6-dimethyl-2-[4-<4-(1-piperidinomethyl)-pyridyl-2-oxy>-cis-2-butenylamino]-4-(1H)-pyrimidone dihydrochloride.

* * * * *